United States Patent [19]

Bergstedt

[11] Patent Number: 4,495,702
[45] Date of Patent: Jan. 29, 1985

[54] CHILD'S GROWTH MEASURING AND REGISTERING DEVICES

[76] Inventor: Lowell C. Bergstedt, 47 Dartmouth St., San Francisco, Calif. 94134

[21] Appl. No.: 411,431

[22] Filed: Aug. 25, 1982

[51] Int. Cl.³ .............................................. G01B 3/00
[52] U.S. Cl. .................................... 33/169 R; 33/161
[58] Field of Search ........... 33/169 R, 143 R, 143 M, 33/173, 161, 168; 211/33, 196, 205; 403/292, 403/296

[56] References Cited

U.S. PATENT DOCUMENTS

| 139,092 | 5/1973 | Urie | 403/292 |
|---|---|---|---|
| 325,134 | 8/1885 | Wainwright | 33/169 R |
| 1,110,968 | 9/1914 | Southard | 33/173 X |
| 1,555,792 | 9/1925 | Souder | 33/143 M |
| 1,974,085 | 9/1934 | Shields et al. | 33/169 R |
| 1,996,553 | 4/1935 | Scully | 33/169 R |
| 2,215,884 | 9/1940 | Runge | 33/169 R |
| 3,196,548 | 7/1965 | Moore | 33/169 R |

FOREIGN PATENT DOCUMENTS

| 1069293 | 1/1980 | Canada | 33/169 R |
|---|---|---|---|
| 2266037 | 10/1975 | France | 403/292 |
| 2379803 | 10/1978 | France | 33/296 |

Primary Examiner—Harry N. Haroian
Attorney, Agent, or Firm—Flehr, Hohbach, Test, Albritton & Herbert

[57] ABSTRACT

The height marking means comprises a generally flat, paddle shaped board having a notch formed in one end thereof adapted to fit around the portion of the stick means with the stick abutting surface being the bottom surface of the notch. The elongated stick is formed in a plurality of sections with arrangements provided for releasably fastening the sections together into a unitary stick assembly. Embodiments including a floor stand or wall mounting brackets are provided. Decals and ruled markings on the stick provide height-age marking on the units.

7 Claims, 21 Drawing Figures

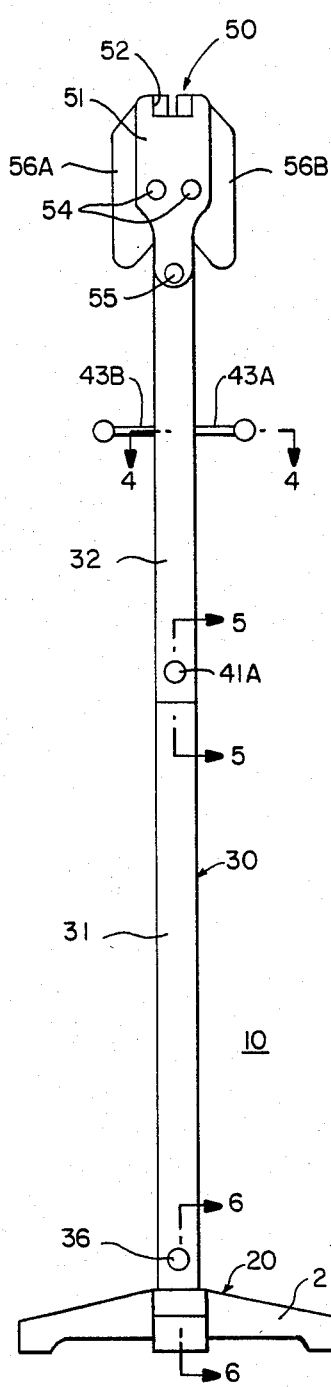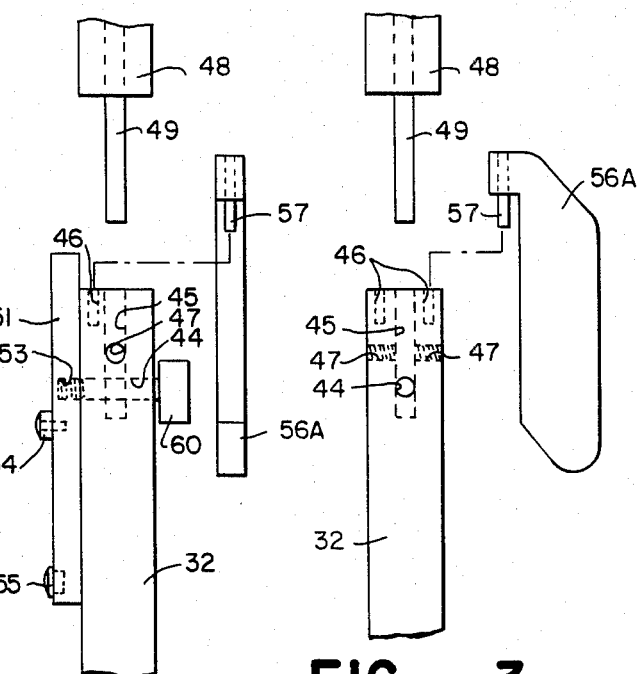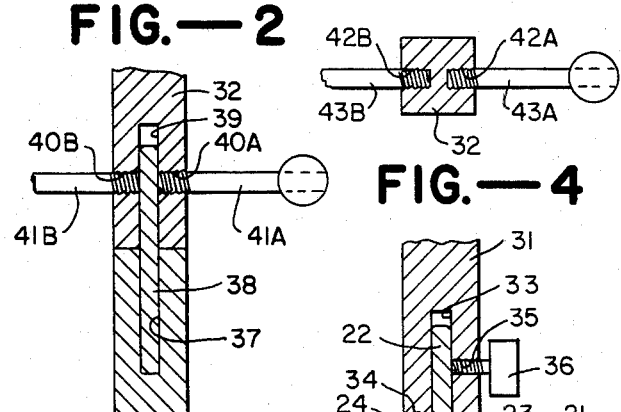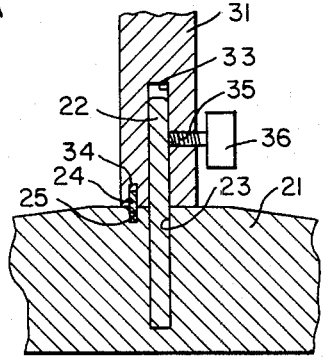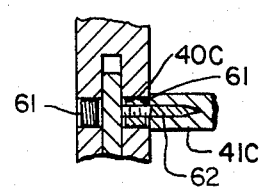
FIG.—1
FIG.—2
FIG.—3
FIG.—4
FIG.—5
FIG.—5A
FIG.—6

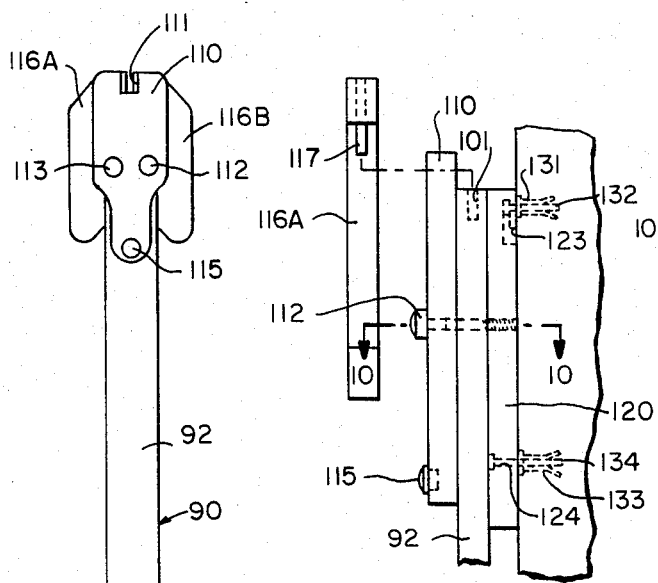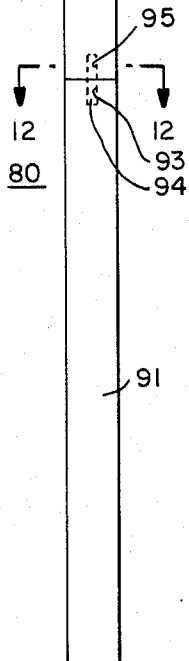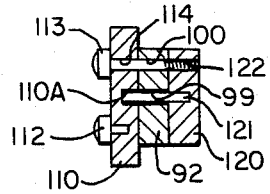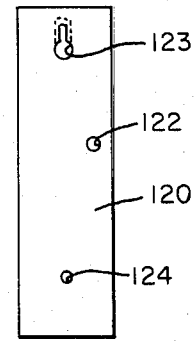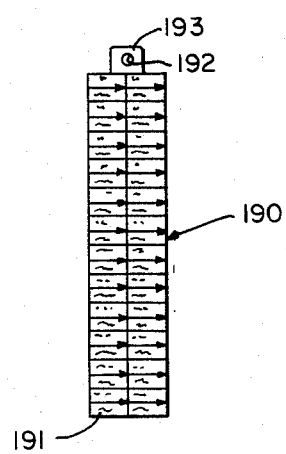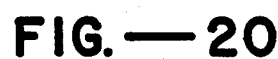
FIG.—7  FIG.—8  FIG.—9  FIG.—10  FIG.—11  FIG.—12  FIG.—20

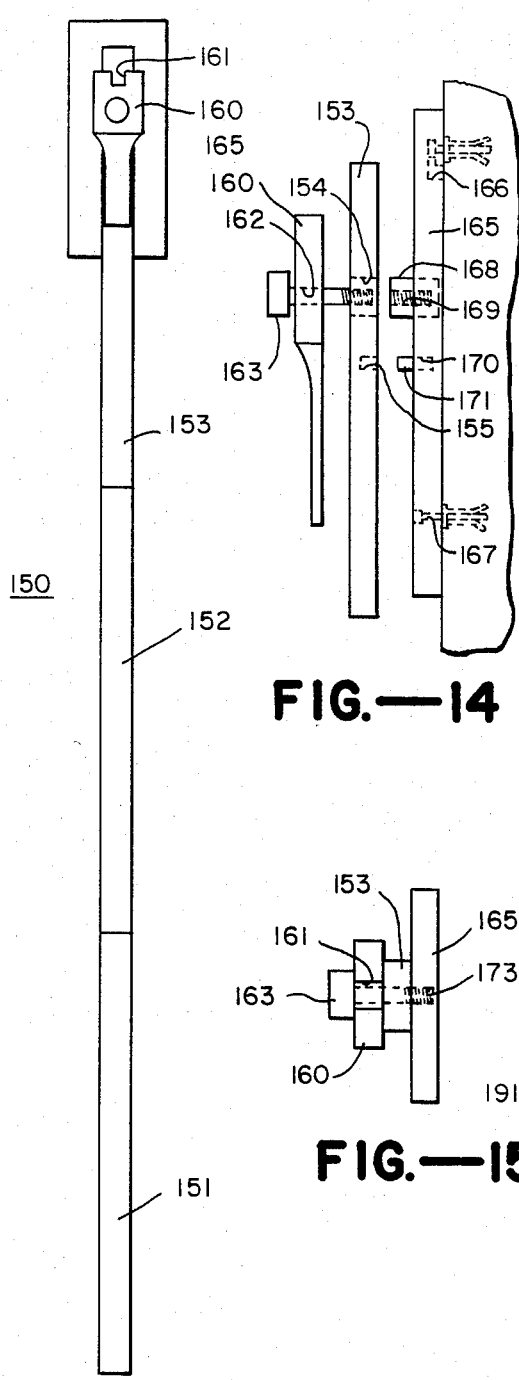
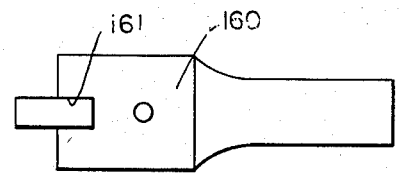
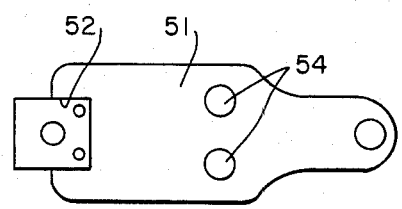
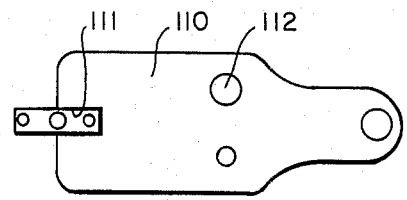
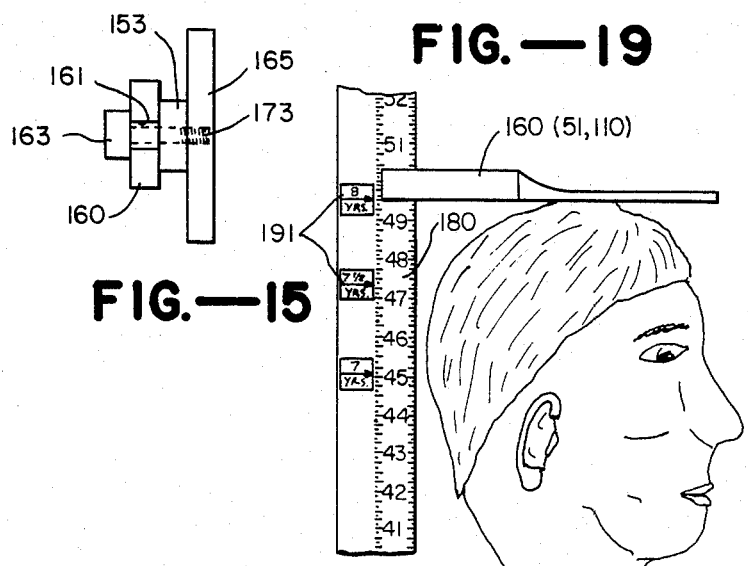

CHILD'S GROWTH MEASURING AND REGISTERING DEVICES

This invention relates generally to growth registering devices for children and, more specifically, to growth measuring and recording units for children.

Most children and their parents have strong interest in the child's growth patterns, for medical and health reasons as well as general curiosity. A number of approaches have been taken in the prior art to providing growth registering devices which actually graphically depict the child's height at various ages. Everyone is familiar with the use of door jams or walls for marking a child's height at various ages. There are also on the market elongated cloth or cardboard sheets on which a child's height can be marked or recorded in some fashion. None of these prior art units provide a convenient, durable, permanent marking of the child's height, nor do they provide a convenient measuring arrangement for accurately gaging the child's height. Marking the height of the child on a door jam and the like does not provide a permanent record and is not a record that is easily transportable if the family moves from one house to another.

Accordingly, it is the principal object of this invention to provide an improved child's growth measuring and registering device.

It is another object of this invention to provide a child's growth measuring and registering device which also serves one or more additional useful functions.

This invention features a growth measuring and indicating unit comprising an elongated stick and a height marking means adapted to be removably mounted to the elongated stick and including a flat stick-abutting surface and a flat gaging surface extending transverse to the stick abutting surface and adapted to contact the head of a child standing next to the stick and thereby to indicate the height of the child on the stick. Preferably the height marking means comprises a generally flat, paddle shaped board having a notch formed in one end thereof adapted to fit around the portion of the stick means with the stick abutting surface being the bottom surface of the notch. It is also preferable that the elongated stick be formed in a plurality of sections and that means be provided for releasably fastening the sections together into a unitary stick assembly.

In one embodiment of the invention, a stand means is provided which is adapted to rest on the floor of a room and includes means for releasably supporting the stick in a vertical position thereon. In this embodiment the height marking means is preferably mounted to a top section of the stick utilizing a threaded aperture means in a broad surface of the height marking means and threaded fastener extending through an aperture in the stick and threadable into the threaded aperture in the height gaging means. It is also preferable that this embodiment include a plurality of clothes supporting means removably mounted to the stick at various selected locations thereon.

In some embodiments of the invention, the paddle shaped board is shaped to resemble a portion of the face of an animal and the unit further comprises a plurality of other animal head portions removably mountable on the stick. In other embodiments, wall bracket means are provided to hang on the wall of a room and means are provided for removably mounting the stick and the height marking means to the wall bracket. In each embodiment of the invention, it is preferable that the elongated stick have a ruled marking on one face thereof for measuring a child's height and that the unit further comprises decal means having a plurality of individual decals with a numerical sequence of ages marked thereon for separately mounting on the ruled face of the stick at the height location indicated by the height marking means while measuring a child. Furthermore, it is preferable that the decal means include an aperture therethrough for removably mounting the decal means to the stick utilizing the same mounting arrangement for mounting the height gaging means thereto.

This invention provides the advantage of a permanent height gaging unit with the height marking means and decal means providing a very convenient way of gaging and marking the height of the child. With the height marking means and the decal means mounted to the stick an integral assembly is provided so these functional units are less likely to be misplaced. Moreover, the height registering and indicating units of this invention are multi-functional.

One unit of the invention doubles as a clothes tree. Other units have the advantage of providing a decorative unit having either animal face sculptural features or general modern art sculptural features.

The units of this invention are conveniently formed from quality hardwoods or softwoods. The preferred embodiments are readily assemblied and disassembled for shipping and for transporting from one home to another if the family moves.

Other objects, features and advantages of this invention will be apparent from a consideration of the following detailed description taken in conjunction with the accompanying drawings.

FIG. 1 is a front elevational view of one embodiment of a child's growth measuring and registering unit in accordance with this invention.

FIG. 2 is a partly exploded side elevational view of a portion of the embodiment of FIG. 1.

FIG. 3 is a partly exploded rear elevational view of a portion of the unit illustrated in FIG. 1.

FIG. 4 is a partial section view taken along the line 4—4 in FIG. 1.

FIG. 5 is a partial section view of a stick assembling arrangement taken along the line 5—5 in FIG. 1.

FIG. 5A illustrates an alternative stick section fastening arrangement to the one depicted in FIG. 5.

FIG. 6 is a partial section view of a stock and base mounting arrangement taken along the line 6—6 in FIG. 1.

FIG. 7 is a front elevational view of another embodiment of a child's growth measuring and registering unit in accordance with this invention.

FIG. 8 is a partly exploded right-side elevational view of a portion of the embodiment of FIG. 7.

FIG. 9 is a partly exploded rear elevational view showing a portion of the embodiment of FIG. 7.

FIG. 10 is a partial section view taken along the lines 10—10 in FIG. 8.

FIG. 11 is a rear elevational view of a wall bracket used in connection with the embodiment of FIG. 7.

FIG. 12 is a section view taken along the line 12—12 in FIG. 7.

FIG. 13 is a front elevational view of another embodiment of a growth measuring and registering unit in accordance with this invention.

FIG. 14 is a partly exploded side elevational view of the stick and bracket arrangement of the embodiment depicted in FIG. 13.

FIG. 15 is a top view of the embodiment of FIG. 13 showing an alternative mounting arrangement.

FIG. 16 illustrates the use of the growth measuring and registering units of this invention to measure the height of a child.

FIG. 17-19 illustrate the functional use of the height-marking means of various embodiments of this invention.

FIG. 20 shows a preferred version of a decal arrangement for use in registering a child's height in accordance with this invention.

Referring now to FIGS. 1-6, an embodiment of this invention which combines a clothes tree with a growth measuring and indicating unit will be described. In addition to these utilitarian functions, the unit has a decorative appearance which is covered in a co-pending U.S. design application Ser. No. 411,491, filed Aug. 25, 1982. Alternative to the dog head design depicted in FIG. 1, a deer head design, as covered in co-pending U.S. design application Ser. No. 411,490, filed Aug. 25, 1982, may also be provided on this combined clothes tree and growth measuring and indicating unit. It will also be apparent that other types of animal head designs and other different designs concepts (e.g. using clown heads, decorative plaques, or crests) could be fashioned using the elements of this invention.

The combined unit 10 includes a base assembly 20, a stick assembly 30 and a height marking gage and mounting assembly 50. A four-legged base 21 is depicted in FIG. 1 and represents only one of many types of stick support bases which could be provided for this unit. The stick assembly 30 includes a lower stick 31 and an upper stick 32. The lower stick 31 is removably mounted to the base 21, utilizing a convenient mounting arrangement such as the one depicted in FIG. 6. In this arrangement a cylindrical dowel is permanently fixed (e.g. by gluing) in an aperture 23 in the base 21 and is removably received in an aperture 33 in the bottom stick section 31. A pin 24 may be fixedly mounted in an aperture 25 in the base 21 to be removably received in an aperture 34 in the bottom stick section 31 to preclude the stick section 31 from revolving on the base 21. A threaded aperture 35 and a threaded wood screw 36 may be used cooperatively to lock the stick section 31 on the base 21. Other locking arrangements such as the one shown in FIG. 5A could also be used.

The two stick sections 31 and 32 may be removably mounted together utilizing the mounting arrangement shown in FIG. 5 or the alternative mounting arrangement shown in FIG. 5A. As shown in FIG. 5 a cylindrical dowel 38 is fixedly mounted in an aperture 37 in the upper portion of the lower stick section 31. The dowel 38 is preferably glued into the aperture 37. The upper stick section 32 has a dowel receiving aperture 39 therein. Cooperative locking means comprising threaded apertures 40A and 40B and threaded dowels 41A and 41B lock the upper stick section 32 to the dowel 38 and thus to the lower stick section 31.

In the alternative version of FIG. 5A, the same dowel 38 is utilized, but a screw collar 61 having external wood screw threads is threaded into an aperture 40C and receives in its internal machine screw threads a combined machine screw and lag screw 62. The lag screw section of the fastener 61 is threaded into a wooden clothes support piece 41C. Other arrangements of clothes hooks and the like as well as other arrangements for utilizing screws and/or metal brackets could be utilized for fastening stick sections 31 and 32 together. The approachs shown in FIGS. 5 and 5A are convenient ones since they provide a clothes mounting function in addition to a locking function for the two stick sections.

Additional clothes mounting capability is provided by the threaded dowels 43A and 43B which are mounted in threaded apertures 42A and 42B in the upper stick section 32. It should be apparent that the same mounting arrangement as shown in FIG. 5A could be substituted for the threaded dowel-threaded aperture approach shown in FIG. 4.

Referring back to FIG. 1, the height gaging or marking means comprises a flat paddle-shaped element 51 having a broad notch 52 formed in the top end thereof. The paddle unit 51 is fashioned into the shape of a dog face having eyes 54 and a nose 55 which may comprise dowels or buttons glued to the top face of the height gaging means mounted with glued dowel sections extending into the top face of the element 51. As shown in FIG. 2, the height gaging means 51 is mounted to the upper stick section 32 utilizing a threaded aperture 53 in the back face of height gaging means 51 together with a threaded fastener 60 which extends through an aperture 44 in the upper stick section 32. Utilizing this arrangement, the height gaging means 51 can be simply screwed tightly to the adjacent surface of the upper stick section 32.

As shown in FIGS. 2 and 3 animal ears such as the dog ears 56A may be removably mounted to the top stick section 32 utilizing dowels 57 which are removably received in apertures 46 formed in the top of the upper stick section. Also as shown in FIGS. 2 and 3, a third stick section 48 may be mounted to the upper stick section 32, utilizing a dowel 49 received in an aperture 45 this increases the height of the stick assembly to measure taller children. The upper portion of the optional additional stick 48 may have the same height marking means and animal ears mounting apertures as provided on stick section 32. Threaded apertures 47 may be provided in the stick section 32 to receive threaded dowels to lock the third stick section 48 to the stick section 32, thereby utilizing the same type of removable fastening arrangement as shown in FIG. 5.

It will be apparent that other types of animal heads including different animal face designs and ear designs may be utilized in this invention. For example, the deer head shown in design patent application Ser. No. 411,490 and referred to above may be utilized as an alternative to the dog head and ear design shown in FIGS. 1-3.

FIGS. 16 and 18 generally depict the manner in which the growth measuring unit shown in FIG. 1-6 may be utilized to measure and register the height of a child. On one of the side faces of the stick assembly 30, a ruled marking 180 in inches or metric units is provided. To measure the child's height, the stick assembly 30 is removed from the base assembly 20 by loosening the locking screw 36. The clothes hanging arms 43A and 43B are then removed from the stick assembly along with the ears 56A and 56B and the height marking paddle 51. The stick assembly 30 is then positioned, with its bottom surface on the floor, against a vertical wall and the child stands next to the stick with the height gaging paddle positioned against the stick as shown in FIGS. 16 and 18. With the bottom surface of the height gaging paddle resting on top of the child's head and the bottom surface of the notch 52 tightly pushed against the abutting surface of the stick, the height gaging means accurately marks the height of the child as shown generally in FIG. 16.

An appropriate one of the peel off decal sections 191 from the decal assembly 190 (FIG. 20) may then be positioned on the surface of the stick at the location marked by the height gaging paddle to register the child's height at the corresponding age. After the marking has been completed the unit can be reassembled into the decorative clothes tree unit shown in FIG. 1.

The stand alone clothes tree unit shown in FIG. 1 is preferably formed from a hardwood material such as beech or alder. It should be apparent that the stick assembly 30 could be formed from a single length of wood, but it is preferable to utilize two separate sections for convenience of packaging the unit for original shipping or for moving from one home to another. Preferably the individual sticks 31 and 32 are each about 26 inches long. The ruled marking on one surface of the stick can be provided by any convenient approach such as utilizing a decal, by using a burn-in stamping die process or by stenciling the ruled markings on the stick.

After the child has outgrown the length of the two sticks 31 and 32 the third stick 48 shown in FIGS. 2 and 3 may be added. For the more mature child, it may be desirable to provide a different type of design for the height marking paddle at the time the third stick 48 is added. Alternatively, other ways of customizing the stand alone unit for the more mature child could be provided. For example, an elongated chalkboard or bulletin board could be removably mounted to the stick assembly utilizing wood screws or other fasteners mounted through the frame of the chalkboard or bulletin board.

Referring now to FIGS. 7-12, a wall mounted growth measuring and indicating unit 80 will be described. The unit 80 utilizes two stick sections 91 and 92 which are preferably about three-quarters of an inch thick and two and one-half inches wide. The two stick sections 91 and 92 of the stick assembly 90 are fastened together using an arrangement of a dowel 94 glued into an aperture 93 in the lower stick section 91 with the dowel 94 removably extending into an aperture 95 in the bottom of the upper stick section 92. A pair of threaded screw collar inserts 97 as shown in FIG. 12 may be mounted in apertures 96 extending through the sides of the stick section 92 with flat head machine screws 98 extending through the threaded insert 97 to press tightly against the dowel 94. This holds the two stick sections 91 and 92 tightly together. Other similar removable fastening arrangements could readily be provided.

As shown in FIGS. 8-11, a combination of a wall bracket 120 and the height marking paddle 110 are utilized to mount the stick assembly 90 and the height marking paddle 110 to a wall. The wall bracket 120 has a screw hanging slot 123 formed in a top portion thereof and screw fastening aperture 124 formed in a bottom portion thereof. The respective wood screws 132 and 134 may be utilized to mount the bracket 120 to a wall utilizing plastic anchors 131 and 133 or other wall anchor arrangements as necessary.

As shown in FIG. 10 a mounting pin 121 is fastened into the wall bracket 120 and extends forward of the bracket to be received in an aperture 99 in the upper stick section 92 and into a partial aperture 110A in the back surface of the height marking paddle 110. An eye piece 113 in the form of a threaded dowel having a head section thereon extends through an aperture 114 in the height marking paddle 110 and a registered aperture 100 in the upper stick portion 92 and threads into a threaded aperture 122 in the wall bracket 120. A dummy eye 112 is mounted to the height marking paddle 110 and cooperates with the threaded dowel piece 113 and the nose piece 115 to assist, along with the shape of the marking paddle 110 to imitate the face of a dog. The height marking paddle 110 also has a notch 111 which serves to enable the height marking paddle 110 to fit partially around one of the stick sections 91 and 92 for height marking purposes as shown in FIG. 19.

As shown in FIGS. 8 and 9 animal ear pieces 116A and 116B are removably mounted to upper stick section 92, utilizing dowels 117, fitting into apertures 101 in the top surface of stick section 92. Other types of animal faces and head parts such as the deer head shown in co-pending U.S. design application Ser. No. 411,490 referenced above could also be utilized in this embodiment.

As shown in FIG. 9, a dowel receiving aperture 102 may be provided in the upper stick section 92 to enable a third stick section to be added to the unit 80 when the child's height exceeds the length of the stick sections 91 and 92. The stick sections 91 and 92 are preferably about twenty-six inches long so that the height of a child up to about seven or eight years of age may be registered thereon.

To utilize the growth measuring and indicating unit 80 shown in FIG. 7, the stick assembly 90 and the height marking paddle 110 are removed from the wall bracket by unscrewing the threaded dowel eye piece 113 and then lifting the paddle 110 and the stick assembly 90 off of the pin 121. The bottom surface of the stick assembly 90 may then be rested on the floor with one edge against the vertical surface of a wall or door jam and the height marking paddle 110 positioned as shown in FIGS. 16 and 19 to enable the height of the child to be measured and marked using a decal means in the manner described above.

The wall mount unit depicted in FIG. 7 may be customized to have additional functions. For example, provisions could be made for hanging small wallet-size picture frames at spaced locations along the length of the stick sections 91 and 92 to enable photographs of the child at various ages to be displayed. Provisions for removably mounting the photographs frames could readily be made so that height measuring and marking could be performed in the manner previously described.

FIGS. 13-15 illustrate another version of a wall mount unit in which the components are configured to have a sculptural appearance for decorative purposes. The wall mount unit 150 includes lower, middle and upper stick sections 151, 152 and 153 which may be mounted together utilizing the same mounting arrangement shown in FIG. 12. In this unit a larger wall bracket 165 is provided and is mounted to a wall utilizing the mounting screw arrangements 166 and 167 similar to those described in the wall mount version of FIG. 7 described above. As shown in FIG. 14, a dowel section 168 having a threaded aperture 169 may be mounted to the wall bracket 165 to cooperate with an aperture 154 in the top stick section 153 to hang the stick assembly on the wall bracket 165. A peg 171 may also be mounted in an aperture 170 of the wall bracket 165 to be received in a partial aperture 155 in the stick section to prevent swinging of the stick assembly on the bracket. The height gaging paddle 160 mounts to the stick assembly and wall bracket utilizing a threaded dowel 163 insertable through a aperture 162 in the height measuring paddle 160. A notch 161 is formed in the height measuring paddle 160 to partially embrace the stick section during the height marking process as described above in connection with FIGS. 16 and 17.

FIG. 15 shows an alternative arrangement for mounting the stick section 153 and the height marking paddle 160 into the wall bracket 165. FIG. 15 is a top view of the components and shows a threaded dowel 163 extending into a threaded aperture 173 in the wall bracket 165. Preferably the mounting peg 170 shown in FIG. 14 would also be provided for hanging the stick on the wall bracket and precluding rotation between the stick assembly and the bracket.

The wall mount unit 150 depicted in FIG. 13 is preferably formed from three stick sections, each about twenty-six inches long to make a total growth measuring stick having a length of about six and one-half feet. The embodiment of FIG. 13 may be formed from various hard or soft woods using varius stick widths and thicknesses but preferably retaining the general proportions between bracket height marking paddle, and stick as shown in FIG. 13.

To utilize the unit 150 to mark a child's height, the stick assembly and height marking paddle 160 are removed from the wall bracket 165 by unscrewing the threaded dowel 163 and then gaging and marking the child's height as depicted in FIGS. 16 and 17 and described above.

FIG. 20 illustrates a decal system 190 having individual peel-off decal pieces 191 having various ages printed thereon for use in registering the measured height of the child at various ages as depicted in FIG. 16. The decal assembly 190 preferably has the configuration shown in FIG. 20 with a top mounting tab 193 having an aperture 192 therein to enable the decal assembly 190 to be mounted to the stick assembly and height marking paddle when these elements are mounted together or are together mounted to a wall bracket. For example in connection with the stand alone unit of FIG. 1, the decal assembly may be mounted behind the upper stick section 32 by fitting the threaded dowel 60 through the aperture 192. In this manner the decal assembly 190 is retained on the stick assembly and is readily available at the next age-height marking time for the child. This reduces the likelihood of losing the decal assembly.

For the unit shown in FIG. 7, the decal assembly 190 may be hung on the peg 121 either in front of or behind the upper stick section 92. In the wall mount unit depicted in FIG. 13, the decal assembly 190 may be mounted between the height marking paddle 160 and the stick section 153 or may be mounted on the peg 171 between the stick section 153 and the bracket 165. It will thus be appreciated that in each instance the decal assembly 190 will be retained with the overall assembly of the other components of the unit and will thus not be misplaced in a drawer or some other location in the house.

While the general concepts and principles of this invention have been described above in connection with several alternative embodiments, it should be understood that numerous modifications could be made without departing from the scope of the invention as claimed in the following Claims.

What is claimed is:

1. In a growth measuring and indicating unit for children, an elongated stick and a height marking means adapted to be removably mounted to said elongated stick and including a flat stick-abutting surface, and a flat gaging surface extending transverse to said stick-abutting surface and adapted to contact the head of a child standing next to said stick and thereby to indicate the height of said child on said stick, said elongated stick comprising a plurality of separate stick sections and means for releasably fastening said stick sections together in end-to-end butting relationship including aligning means cooperatively engaging adjacent stick sections to maintain vertical alignment therebetween, said unit further comprising stand means adapted to rest on the floor of a room and means for releasably securing said stick to said stand means, including aligning means for maintaining said stick in a vertical upright orientation on said stand means, said height marking means comprising a generally flat, paddle shaped board having a threaded means in one broad surface thereof, said stick having an aperture through a top section thereof, and said unit further comprises a threaded fastener adapted to extend through said aperture in said stick and to thread into said threaded means in said height marking means to mount said height marking means to said stick.

2. Apparatus as claimed in claim 1, wherein said height marking means comprises a generally flat, paddle shaped board having a notch formed in one end thereof adapted to fit at least partially around an edge portion of said stick with said stick-abutting surface being the bottom surface of said notch.

3. Apparatus as claimed in claim 1, further comprising a plurality of clothes supporting arm means removably mounted to said stick at various selected locations thereon.

4. Apparatus as claimed in claim 1, wherein said paddle shaped board is shaped to resemble a portion of the face of an animal and includes at least eye and nose pieces mounted thereto, and said unit further comprises a plurality of other animal head portions such as animal ears removably mounted on said stick.

5. In a growth measuring and indicating unit for children, an elongated stick and a height marking means adapted to be removably mounted to said elongated stick and including a flat stick-abutting surface, and a flat gaging surface extending transverse to said stick-abutting surface and adapted to contact the head of a child standing next to said stick and thereby to indicate the height of said child on said stick, said elongated stick comprising a plurality of separate stick sections and means for releasably fastening said stick sections together in end-to-end butting relationship including aligning means cooperatively engaging adjacent stick sections to maintain vertical alignment therebetween, and further comprising a wall bracket adapted to hang on the wall of a room and means for removably mounting said stick and said height marking means to said wall bracket including a threaded aperture formed in a front surface of said bracket, respectively aligned apertures in said stick and said height marking means, and a threaded fastener adapted to extend through said apertures and thread into said threaded aperture.

6. Apparatus as claimed in claim 5, wherein said height marking means is shaped to resemble a portion of the face of an animal and includes at least eye and nose pieces mounted thereto, and said unit further comprises a plurality of other animal head portions such as animal ears removably mountable on said stick.

7. In a growth measuring and indicating unit for children, an elongated stick and a height marking means adapted to be removably mounted to said elongated stick and including a flat stick-abutting surface, and a flat gaging surface extending transverse to said stick-abutting surface and adapted to contact the head of a child standing next to said stick and thereby to indicate the height of said child on said stick, said elongated stick comprising a plurality of separate stick sections and means for releasably fastening said stick sections together in end-to-end butting relationship including aligning means cooperatively engaging adjacent stick sections to maintain vertical alignment therebetween, said elongated stick has a ruled marking on one face thereof for measuring a child's height, said height marking means is removably mounted to said stick with a threaded fastener and said unit further comprises decal means having a plurality of individual separable decals with a numerical sequence of ages printed thereon for separately mounting on said ruled face of said stick at a height location indicated by said height marking means, said decal means including an aperture therethrough for removably mounting said decal means to said stick using said threaded fastener.

* * * * *